US012773468B2

(12) United States Patent
Agrawal et al.

(10) Patent No.: US 12,773,468 B2
(45) Date of Patent: Oct. 27, 2026

(54) BIODEGRADABLE DISPOSABLE DIAPER WITH FUNGAL REACTANTS

(71) Applicant: Hiro Technologies, Inc., Austin, TX (US)

(72) Inventors: Miki Agrawal, Austin, TX (US); Tero Isokauppila, Austin, TX (US)

(73) Assignee: Hiro Technologies, Inc., Austin, TX (US)

( * ) Notice: Subject to any disclaimer, the term of this patent is extended or adjusted under 35 U.S.C. 154(b) by 653 days.

(21) Appl. No.: 17/950,722

(22) Filed: Sep. 22, 2022

(65) Prior Publication Data

US 2023/0086964 A1 Mar. 23, 2023

Related U.S. Application Data

(60) Provisional application No. 63/247,193, filed on Sep. 22, 2021.

(51) Int. Cl.
*A61L 15/36* (2006.01)
*A61L 15/62* (2006.01)

(52) U.S. Cl.
CPC ............... *A61L 15/36* (2013.01); *A61L 15/62* (2013.01)

(58) Field of Classification Search
CPC .......... A61L 15/36; A61L 15/62; A61L 15/38; A61L 15/16; A61F 13/15252;

(Continued)

(56) References Cited

U.S. PATENT DOCUMENTS 4,944,734 A 7/1990 Wallach
5,300,358 A * 4/1994 Evers ...................... A61L 15/24 604/382

(Continued)

FOREIGN PATENT DOCUMENTS

JP 2003265522 A 9/2003
WO 0061201 A1 10/2000

OTHER PUBLICATIONS

Rosa María Espinosa-Valdemar, Sylvie Turpin-Marion, Irma Delfín-Alcalá, Alethia Vázquez-Morillas, Disposable diapers biodegradation by the fungus Pleurotus ostreatus, Waste Management, 2011, pp. 1683-1688, vol. 31, Issue 8, 2011, ISSN 0956-053X, https://doi.org/10.1016/j.wasman.2011.03.007. (https://www.sciencedirect.com/science/article/pil/S0956053X11001218).

(Continued)

*Primary Examiner* — Rebecca E Eisenberg
*Assistant Examiner* — Gabriella E Burnette
(74) *Attorney, Agent, or Firm* — Alix, Yale & Ristas, LLP

(57) ABSTRACT

A biodegradable disposable diaper includes an inner layer comprising a soft, non-woven fabric, the inner layer for resting against a wearer's skin and allowing the passage of bodily waste fluids, a middle layer comprising superabsorbent polymer for absorbing and retaining the bodily waste fluids, an outer layer comprising a liquid impermeable membrane, the outer layer for restricting the passage of bodily waste fluids, and a frangible capsule, dispenser or packet containing a substance comprising mycelium, fungal spores and/or enzymes configured for using bodily waste to grow and degrading the biodegradable disposable diaper in a disposal environment, the frangible capsule, dispenser or packet further for allowing the deposition of the substance into the diaper at the time of disposal. A substance configured for using bodily waste to grow and degrading a (Continued)

biodegradable disposable diaper in a disposal environment, the substance configured for deposition onto the diaper.

19 Claims, 4 Drawing Sheets

(58) Field of Classification Search
CPC ............ A61F 13/49; A61F 2013/51035; A61F 2013/51433; A61F 2013/530313; A61F 2013/530795; A61F 2013/53481; A61F 2013/8438
See application file for complete search history.

(56) References Cited

U.S. PATENT DOCUMENTS 7,928,282 B2 4/2011 Dibb et al.
2006/0030023 A1* 2/2006 Somers .................. C02F 3/342 435/262.5
2008/0046277 A1* 2/2008 Stamets ................. G06Q 90/00 705/308
2010/0104615 A1 4/2010 Jiffer
2015/0038326 A1 2/2015 Araldi et al.
2019/0111176 A1 4/2019 Serna

OTHER PUBLICATIONS

Combined Search and Examination Report dated Apr. 27, 2023 for the United Kingdom Patent Application No. GB2217265.4.
Nemergut, Dr et al., “Benzo[a]pyrene removal by Marasmiellus troyanus in soil microcosms,” J. Industrial Microbiology & Biotechnology, 25, 116-119, 2000.
European Search Report dated Sep. 6, 2023 for European Patent Application No. 22214962.7.
Srikanth, Munuru et al., “Biodegradation of plastic polymers by fungi: a brief review,” Bioresources and Bioprocessing, 9:42 (2022).

* cited by examiner

BIODEGRADABLE DISPOSABLE DIAPER WITH FUNGAL REACTANTS

CROSS-REFERENCE TO RELATED APPLICATIONS

This patent application claims priority to provisional patent application No. 63/247,193 filed Sep. 22, 2021 and titled "Biodegradable Disposable Diaper." The subject matter of patent application No. 63/247,193 is hereby incorporated by reference in its entirety.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

FIELD OF THE INVENTION

The invention disclosed broadly relates to the field of fluid absorbent articles, and more particularly relates to the field of diapers and other personal waste disposal items.

BACKGROUND OF THE INVENTION

A diaper is a type of underwear that allows the wearer to urinate or defecate without using a toilet, by absorbing or containing waste products to prevent soiling of outer clothing or the external environment. When diapers become wet or soiled, they require changing. Most diapers are made of synthetic disposable materials that can be discarded after a single use.

Due to the widespread use of disposable diapers, large quantities of disposable infant diapers are discarded each year and the disposal of these products is a problem. Most of the commercially available disposable diapers consist largely of plastics based on polypropylene and polyethylene which do not break down in the environment, since they resist biodegradation. The average disposable diaper can take hundreds of years to decompose and contains petroleum, plastics, perfumes, wood pulp, and dioxins. Even though a typical disposable diaper consists of a substantial number of biodegradable materials, e.g., wood pulp fibers, and the like, there is a need for reducing the amount of non-biodegradable materials in disposable diapers. There is also a need for speeding up the decomposition time of disposable diapers in landfills.

Therefore, a need exists to overcome the problems with the prior art as discussed above, and particularly for a more effective, environmentally friendly, and efficient disposable diaper.

SUMMARY OF THE INVENTION

The claimed subject matter improves over the prior art by providing a biodegradable disposable diaper. This Summary is provided to introduce a selection of disclosed concepts in a simplified form that are further described below in the Detailed Description including the drawings provided. This Summary is not intended to identify key features or essential features of the claimed subject matter. Nor is this Summary intended to be used to limit the claimed subject matter's scope.

Briefly, according to one embodiment, a biodegradable disposable diaper includes an inner layer comprising a soft, non-woven fabric, the inner layer configured for resting against a wearer's skin and allowing the passage of bodily waste fluids, a middle layer comprising superabsorbent polymer for absorbing and retaining the bodily waste fluids that have passed through the inner layer, an outer layer comprising a liquid impermeable membrane, the outer layer configured for restricting the passage of bodily waste fluids, and a frangible capsule, dispenser or packet containing a substance comprising mycelium, fungal spores and/or enzymes configured for using bodily waste to grow and degrading the biodegradable disposable diaper in a disposal environment, the frangible capsule, dispenser or packet further configured for allowing the deposition of the substance into the diaper at the time of disposal. In another embodiment, a substance comprising mycelium, fungal spores and/or enzymes is configured for using bodily waste to grow and degrading a biodegradable disposable diaper in a disposal environment, the substance configured for deposition onto the diaper at the time of disposal.

Additional aspects of the disclosed embodiment will be outlined in part in the description that follows or will be evident in part from the description or learned by practicing the dis-closed embodiments. The aspects of the disclosed embodiments will be attained by means of the elements and combinations particularly pointed out in the appended claims. It is to be understood that both the foregoing general description and the following detailed description are exemplary and explanatory only and are not restrictive of the disclosed embodiments, as claimed.

BRIEF DESCRIPTION OF THE DRAWINGS

The accompanying figures, which are incorporated in and constitute part of this specification, illustrate embodiments of the claimed subject matter and, together with the description, explain the disclosed embodiments' principles. The embodiments illustrated herein are examples. It is understood, however, that the claimed subject matter is not limited to the precise arrangements and instrumentalities shown, wherein:

DETAILED DESCRIPTION

Figure 1:
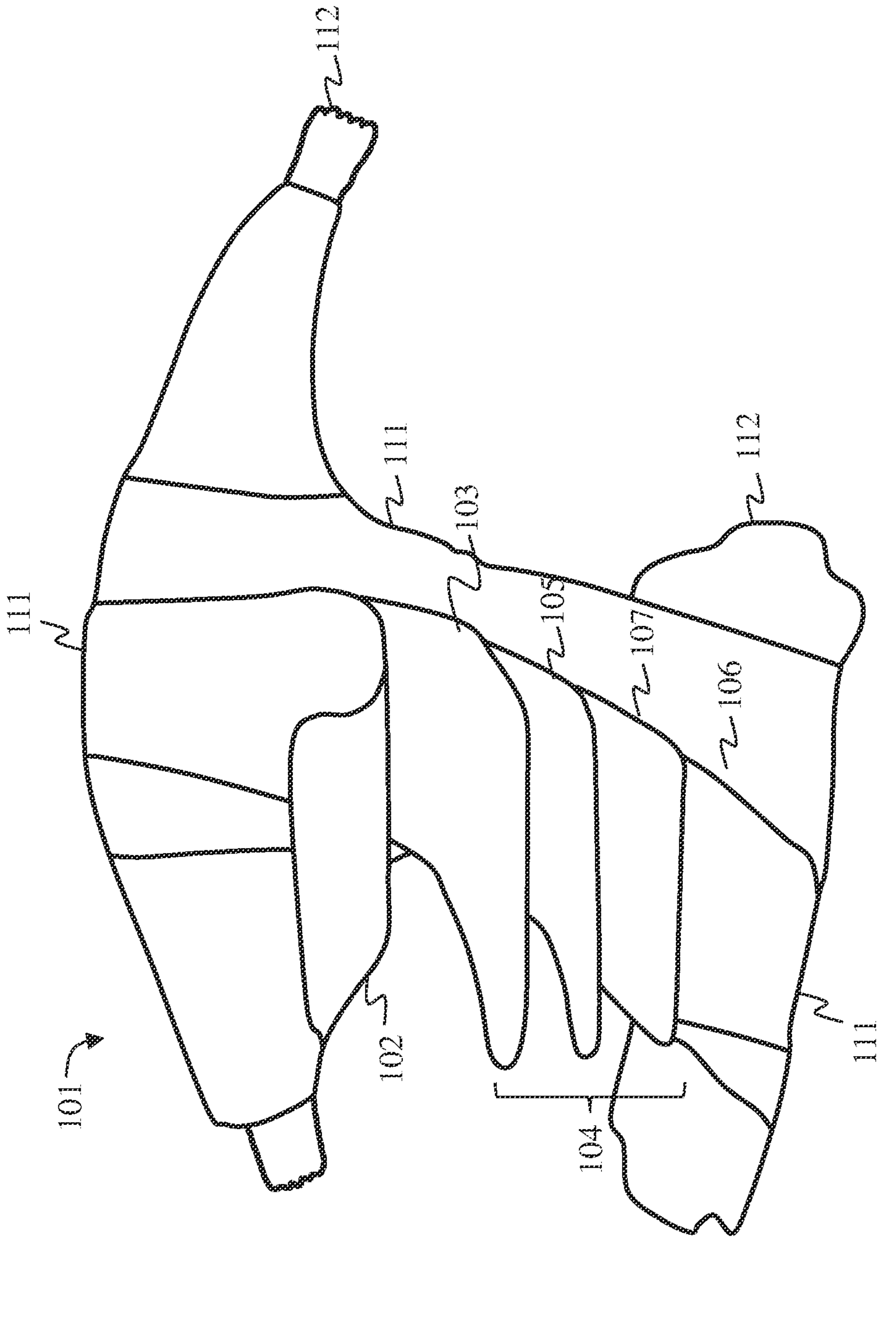
FIG. 1 is a perspective and partially exploded view of a biodegradable disposable diaper of a biodegradable disposable diaper with fungal reactants, in accordance with one embodiment.

The following detailed description refers to the accompanying drawings. Wherever possible, the same reference numbers are used in the drawings and the following description to refer to the same or similar elements. While embodiments may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the claimed subject matter. Instead, the proper scope of the claimed subject matter is defined by the appended claims.

The claimed subject matter improves over the prior art by providing an improved biodegradable disposable diaper with increased biodegradable properties, while still accomplishing the task of absorbing or containing bodily waste products to prevent soiling of outer clothing or the external environment. Applicant's claimed embodiments further address problems with the prior art in disposable diapers by implementing a system that not only results in the quicker biodegradability of the instant diaper but that also increases the biodegradability of other plastic trash in its vicinity in a landfill or garbage dump. From an ethical standpoint, the claimed embodiments offer environmentally friendly features that result in the quicker degradation of waste materials and aids the environment. From a practical standpoint, the claimed embodiments result in lesser amounts of waste material in landfills and garbage dumps, as well as decreasing amounts of greenhouse gasses.

The claimed subject matter will now be described with reference to the figures. FIG. 1 is a perspective and partially exploded view of a biodegradable disposable diaper 101 of a biodegradable disposable diaper with fungal reactants, in accordance with one embodiment. Disposable biodegradable diaper 101 includes an inner layer 102 or top sheet that sits next to the baby's skin and serves as the initial layer that contacts waste fluids. The inner layer 102 may be composed of a soft, non-woven fabric that does not irritate or harm the child's skin. The inner layer 102 allows for the passage of bodily waste fluids, such as urine and fecal liquid, as well as solids, such as fecal matter, onto the next layer, or the middle layer.

Next, the disposable biodegradable diaper 101 includes a middle layer 104 comprising a superabsorbent polymer for absorbing and retaining the bodily waste liquids that have passed through the inner layer 102. The middle layer 104 may include an absorbent core 103 that absorbs and holds the fluids. The absorbent core 103 may be composed of fluff made from wood pulp fibers or corn/wheat-based materials and may include superabsorbent polymer crystals that are dispersed throughout the fluff such that the fluff serves to distribute the fluid. The superabsorbent polymer crystals (also called slush powder) are a water-absorbing polymer that can absorb and retain extremely large amounts of a liquid relative to its own mass. The superabsorbent polymer crystals are intended to absorb the fluid and lock it in the core away from the wearer or the baby. The middle layer 104 may further comprise a breathable film or films 105, 107 located between the layer 103 and the layer 106.

The disposable biodegradable diaper 101 further includes a water impermeable membrane and waterproof outer layer 106 that does not permit the passage of solids, liquids, or gases. The outer layer 106 may be composed of a petroleum-based plastic or plastic-treated material. The outer layer 106 may alternatively be composed of plant-based plastic (such as bioplastic). The outer layer 106 may also comprise a film barrier that acts as a fluid barrier for leak proofing the diaper.

The disposable biodegradable diaper 101 may further include elastic elements 111 to fit the diaper snugly around the legs of the wearer, as well as fasteners 112 required to secure the diaper in place. Said elastic elements are usually polyurethane, polyester foam elastics, or synthetic rubber or elastane (polyether-polyurea copolymer) elastics. Elastane elastics are soft and can be highly efficient. Said elastics can stretch as much as 400% of its original length before breaking. Said elastics may be used in the leg cuff area of the diaper, and also near the waist to give a better fit to the thighs and hip of the wearer. Said elastics may also be used at the side panels of the diaper and also near the fastening tape area, to provide elasticity at the fastening zone of the diaper. Fastener tapes used in the diaper can be hook and loop tape type fasteners or stick tape type fasteners. Hook and loop tape type fasteners give a good mechanical grip, and a strong closure. Stick tape type fasteners are usually made of sticky polypropylene lateral tape which is closed to the polypropylene frontal tape. The disposable biodegradable diaper may further include fungal reactants embedded within one of the layers of the diaper.

Figure 2:
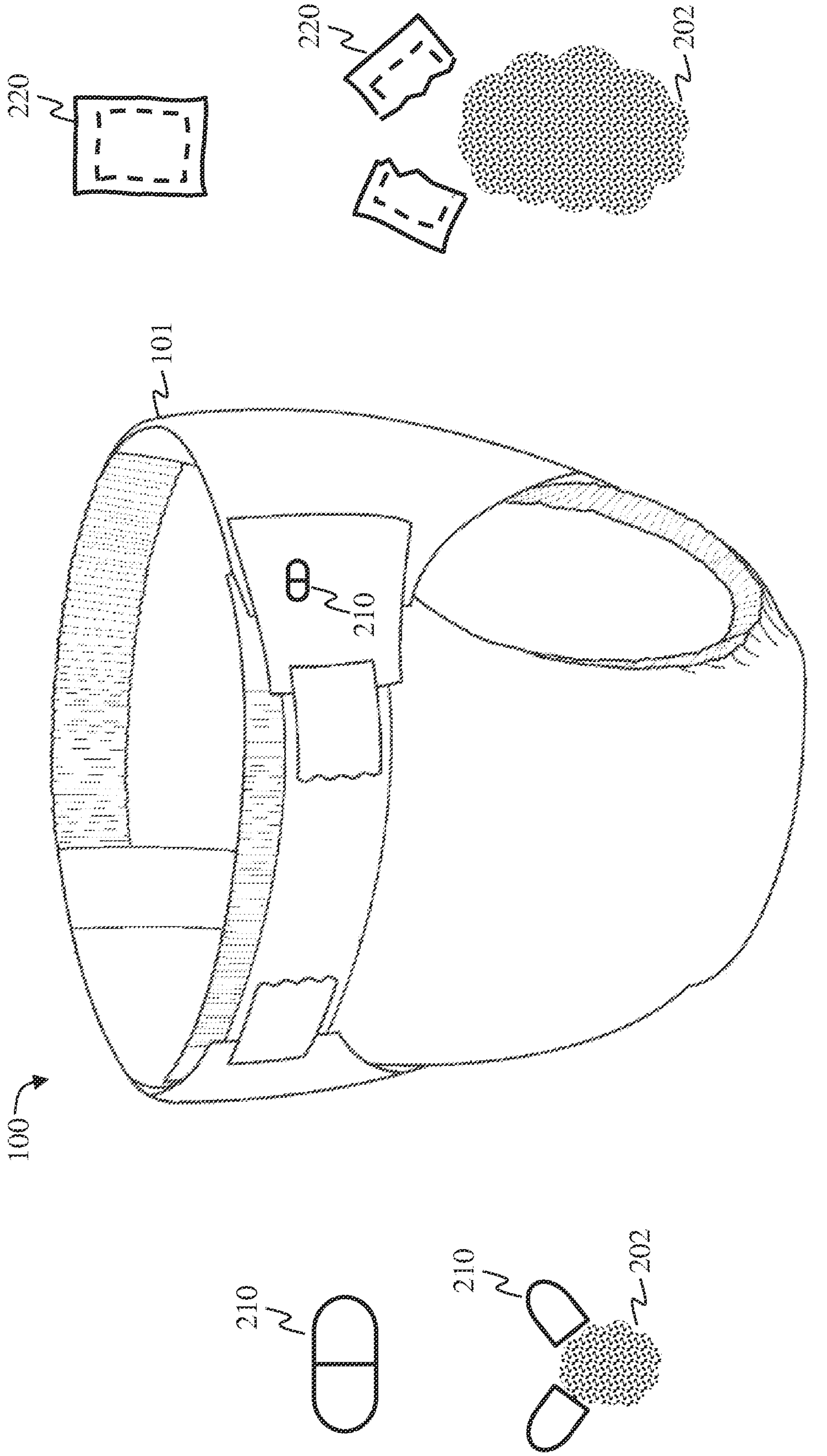
FIG. 2 is a perspective view of the biodegradable disposable diaper with fungal reactants in closed orientation, in accordance with one embodiment.

FIG. 2 is a perspective view of the biodegradable disposable diaper with fungal reactants 100 in closed orientation, in accordance with one embodiment. FIG. 2 shows that the diaper 101, which has been closed as occurs when it is worn on a user, may have attached to its hip area a capsule 210. The capsule 210 may be attached to the diaper using an adhesive or a plastic snap loop, as is often used for retail hanging tags. The capsule 210 may be configured to be frangible and easily broken using manual force. The capsule 210 may include within it a material or substance 202 that is configured for using bodily waste to grow and for degrading the biodegradable disposable diaper in a disposal environment, such as in a landfill or a garbage dump. Note the diaper may be fully biodegradable, meaning that 100% of the diaper, the entire diaper, or fully all aspects and elements of the diaper are biodegradable. The material or substance 202 may comprise mycelium, fungal spores and/or enzymes. Mycelium is the vegetative part of a fungus or fungus-like bacterial colony, consisting of a mass of branching, thread-like hyphae. Through the mycelium, a fungus absorbs nutrients from its environment. A spore is a unit of sexual or asexual reproduction that may be adapted for dispersal and for survival, often for extended periods of time, in unfavorable conditions. A spore is part of the life cycle of fungi. A typical single fungal spore germinates into a monokaryotic mycelium, which cannot reproduce sexually. When two compatible monokaryotic mycelia join and form a dikaryotic mycelium, that mycelium may form fruiting bodies such as mushrooms. A mycelium may be minute, forming a colony that is too small to see, or may grow to a large size. Enzymes are proteins that act as biological catalysts, otherwise known as biocatalysts, which accelerate chemical reactions.

The mycelium and/or fungal spores are configured to utilize the bodily waste in the diaper (such as feces and/or urine) as fuel to grow and subsequently said mycelium and/or fungal spores are configured for degrading the diaper when it is in a landfill or a garbage dump. Said mycelium and/or fungal spores are further configured for degrading plastics and other materials surrounding the diaper, or in the vicinity of the diaper, in the landfill or garbage dump. The enzymes are also configured for degrading the diaper when it is in a landfill or a garbage dump, and for degrading plastics and other materials surrounding the diaper, or in the vicinity of the diaper, in the landfill or garbage dump.

The material or substance 202, which may comprise mycelium, fungal spores and/or enzymes, may be in the form of beads, fabric on which said material or substance has been deposited (in the form of an encapsulated pellet), or in a powder form that may or may not deposited onto a substrate. In one embodiment, the material or substance 202 is embedded in the diaper 100.

FIG. 2 also shows that the capsule 210 may be easily broken so as to allow the material or substance 202 to fall out of the capsule. The diaper 100 is configured to be used in the following way: after the diaper 101 has been soiled but before it is disposed, the capsule 210 is broken and the material or substance 202 is deposited into the interior of the diaper such that the material or substance may react with the bodily waste or fluids within the diaper. Subsequently, the diaper may be disposed of.

FIG. 2 also shows that a packet 220 may be coupled to, or otherwise associated with, the diaper 101. The packet 220 may be attached to the diaper using an adhesive or a plastic snap loop, as is often used for retail hanging tags. The packet 220 may be configured to be easily torn using manual force. The packet 220 may include within it the material or substance 202.

The FIG. 2 shows that the packet 220 may be easily torn so as to allow the material or substance 202 to fall out of the packet. The diaper 100 is configured to be used in the following way: after the diaper 101 has been soiled but before it is disposed, the packet 220 is broken and the material or substance 202 is deposited into the interior of the diaper such that the material or substance may react with the bodily waste or fluids within the diaper. Subsequently, the diaper may be disposed of.

Figure 3:
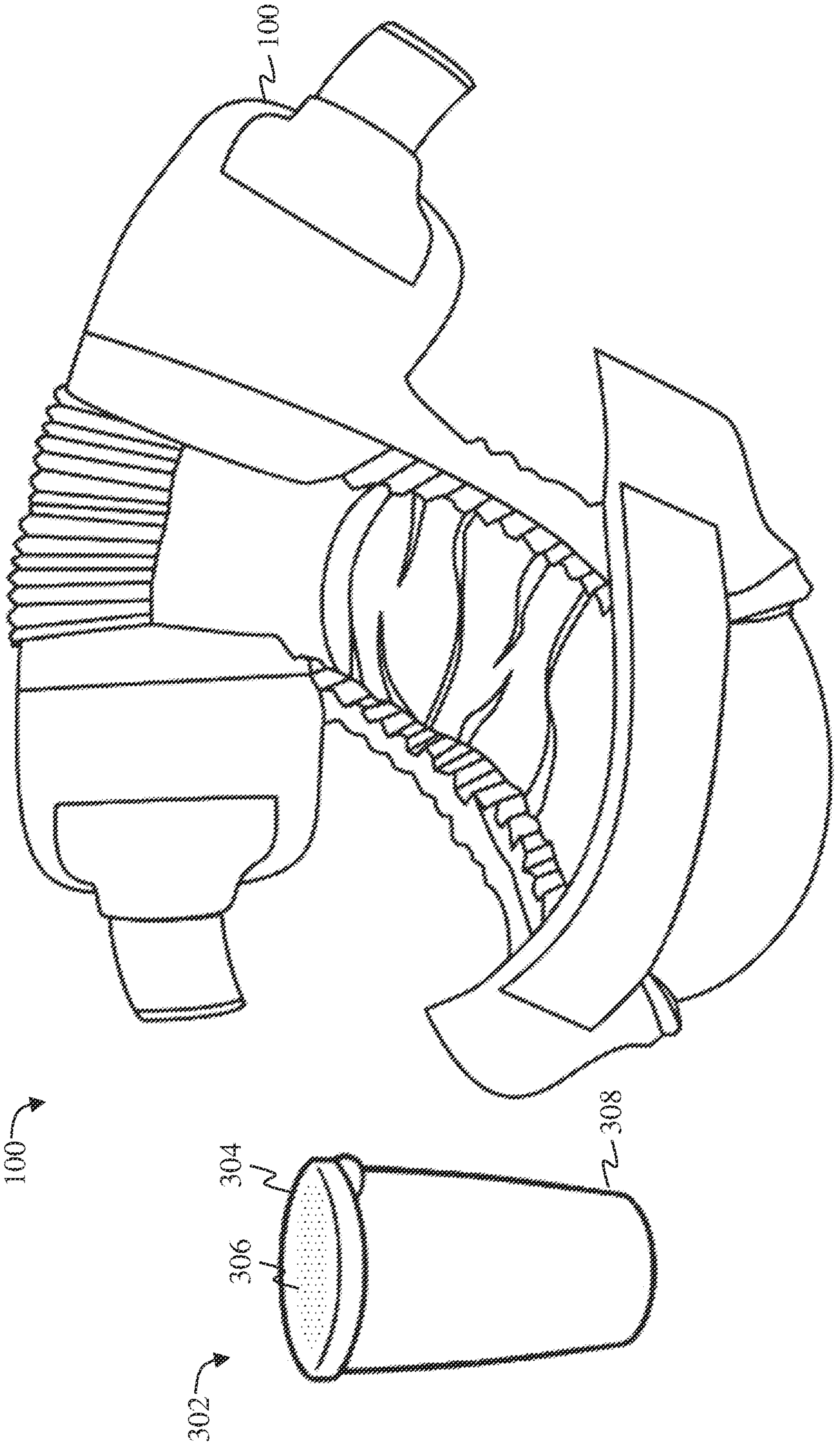
FIG. 3 is a perspective view of the biodegradable disposable diaper with fungal reactants with dispenser and in open orientation, in accordance with one embodiment.

FIG. 3 is a perspective view of the biodegradable disposable diaper with fungal reactants 100 with dispenser 302 and in open orientation, in accordance with one embodiment. FIG. 3 also shows that a dispenser 302 may be coupled to, or otherwise associated with, the diaper 101, which is open as occurs after use of the diaper. The dispenser 302 may be attached to the diaper using an adhesive or a plastic snap loop, as is often used for retail hanging tags. The dispenser 302 may comprise a container 308, a top 304 and perforations 306 in said top. The container 308 may include within it the material or substance 202.

Figure 4:
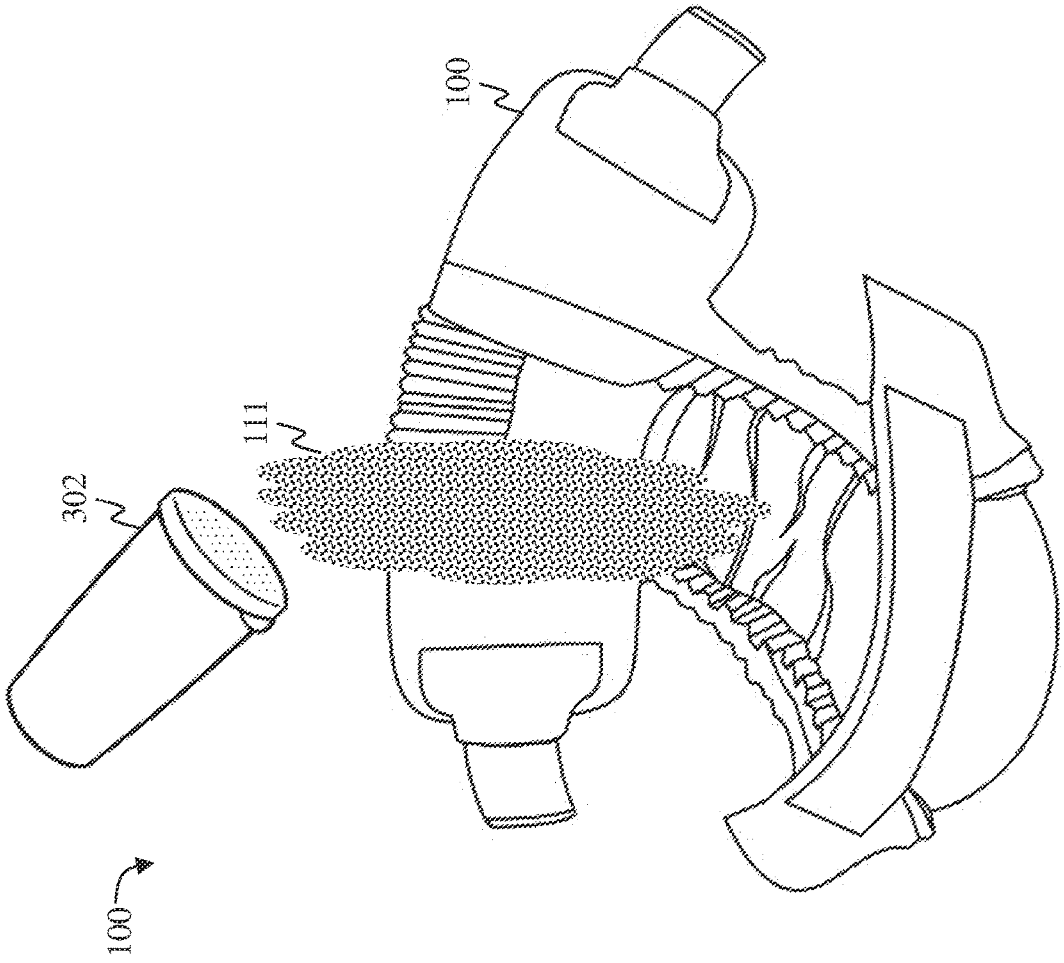
FIG. 4 is a perspective view of a biodegradable disposable diaper with fungal reactants with dispenser in use and in open orientation, in accordance with one embodiment.

FIG. 4 is a perspective view of a biodegradable disposable diaper 100 with dispenser 302 in use and in open orientation, in accordance with one embodiment. The FIG. 4 shows that the dispenser 302 may be shaken or moved over the diaper 101 so as to allow the material or substance 202 to fall out of the container. Optionally, the dispenser may be punch activated wherein a button is clicked on the dispenser and pellets are released. The diaper 100 is configured to be used in the following way: before or after the diaper 101 has been soiled but before it is disposed, the dispenser 302 is shaken over the diaper and the material or substance 202 is deposited into the interior of the diaper such that the material or substance may react with the bodily waste or fluids within the diaper. Subsequently, the diaper may be disposed of.

Also disclosed is a substance comprising mycelium, fungal spores and/or enzymes configured for using bodily waste to grow and degrading a biodegradable disposable diaper in a disposal environment, the substance configured for deposition onto the diaper at the time of disposal. The substance may comprise a plurality of mycelium beads, a fabric on which mycelium has been deposited or mycelium in a powder form, among other things.

Although specific embodiments of the claimed embodiments have been disclosed, those having ordinary skill in the art will understand that changes can be made to the specific embodiments without departing from the spirit and scope of the claimed embodiments. The scope of the claimed embodiments is not to be restricted, therefore, to the specific embodiments. Furthermore, it is intended that the appended claims cover any and all such applications, modifications, and embodiments within the scope of the claimed embodiments.

Embodiments herein, for example, are described above with reference to illustrations of devices and apparatuses, according to said embodiments. While certain embodiments have been described, other embodiments may exist. Although the subject matter has been described in language specific to structural features, it is to be understood that the subject matter defined in the appended claims is not necessarily limited to the specific features or acts described above. Rather, the specific features and acts described above are disclosed as example forms of implementing the claims.

What is claimed is:

1. A biodegradable disposable fluid absorbent article, comprising:
- an inner layer comprising a non-woven fluid permeable fabric;
- a fluid absorbent middle layer comprising a polymer;
- a fluid impermeable outer layer; and
- a composition comprising one or more mycelium, fungal spores, or combinations thereof configured for reacting with bodily waste to initiate growth of the mycelium, fungal spores or both, and to degrade the inner layer, middle layer and outer layer of the biodegradable disposable fluid absorbent article, wherein the composition is configured for deposition onto the biodegradable disposable fluid absorbent article after the absorbent article is used.

2. The biodegradable disposable fluid absorbent article of claim 1, wherein the composition comprises a plurality of mycelium beads, fabric on which mycelium has been deposited or mycelium in a powder form, or is contained in a frangible capsule.

3. The biodegradable disposable fluid absorbent article of claim 1, wherein said composition is contained in a frangible capsule that is coupled to the fluid absorbent article via a plastic snap loop or via an adhesive.

4. A biodegradable disposable fluid absorbent article kit, comprising:
- a biodegradable disposable fluid absorbent article comprising
- an inner layer comprising a non-woven fluid-permeable fabric;
- a fluid-absorbent middle layer comprising a polymer;
- a fluid-impermeable outer layer; and
- a dispenser containing a composition comprising one or more mycelium, fungal spores or combinations thereof configured for reacting with bodily waste to initiate growth and degrade the inner layer, middle layer and outer layer of the biodegradable disposable fluid absorbent article, wherein
- the dispenser is configured for being opened and handled to allow deposition of the composition into the biodegradable disposable fluid absorbent article after the biodegradable disposable fluid absorbent article is soiled with bodily waste.

5. The biodegradable disposable fluid absorbent article kit of claim 4, wherein the composition comprises a plurality of mycelium beads, a fabric on which mycelium has been deposited or mycelium in powdered form.

6. The biodegradable disposable fluid absorbent article kit of claim 4, wherein said dispenser is a disposable container with a perforated top.

7. A biodegradable disposable fluid absorbent article, comprising:

an inner layer comprising a non-woven fluid permeable fabric;

a fluid-absorbent middle layer comprising a polymer;

a fluid-impermeable outer layer; and a packet containing a composition comprising one or more mycelium, fungal spores, or combinations thereof configured for reacting with bodily waste to initiate growth of the mycelium, fungal spores or both, and to degrade the inner layer, middle layer and outer layer of the biodegradable disposable fluid absorbent article, wherein the composition is configured for deposition onto the biodegradable disposable fluid absorbent article after the absorbent article is used.

8. The biodegradable disposable fluid absorbent article of claim 7, wherein said composition comprises a plurality of mycelium beads, fabric on which mycelium has been deposited or mycelium in a powder form.

9. A composition comprising mycelium, fungal spores, or combinations thereof configured for reacting with bodily waste to initiate growth of the mycelium, fungal spores or both, and to degrade a biodegradable disposable fluid absorbent article with (a) an inner layer comprising a non-woven fluid permeable fabric, (b) an absorbent middle layer comprising a polymer, and (c) a liquid impermeable outer layer, wherein the composition is configured for deposition onto the biodegradable disposable fluid absorbent article after the biodegradable disposable fluid absorbent article is used.

10. The composition of claim 9, wherein said composition comprises one or more of the groups consisting of: a plurality of mycelium beads, a fabric on which mycelium has been deposited, and mycelium in a powder form.

11. The biodegradable disposable fluid absorbent article of claim 7, wherein the packet is configured for being opened and handled via human action to allow the deposition of the one or more mycelium, fungal spores, or combinations thereof into the biodegradable disposable fluid absorbent article at a time of disposal.

12. The biodegradable disposable fluid absorbent article of claim 1, wherein the frangible capsule is configured for being broken via human action to allow deposition of the one or more mycelium, fungal spores, or combinations thereof into the biodegradable disposable fluid absorbent article at the time of disposal.

13. The biodegradable disposable fluid absorbent article of claim 1, wherein the polymer is a super absorbent polymer (SAP).

14. The biodegradable disposable fluid absorbent article of claim 1, wherein the composition further comprises one or more enzymes.

15. The biodegradable disposable fluid absorbent article of claim 1, wherein the composition is in an encapsulated form.

16. The biodegradable disposable fluid absorbent article of claim 1, wherein the composition is configured for using the bodily waste to grow and for degrading the biodegradable disposable fluid absorbent article.

17. The biodegradable disposable fluid absorbent article kit of claim 4, wherein the polymer is a super absorbent polymer (SAP).

18. The biodegradable disposable fluid absorbent article kit of claim 4, wherein the composition further comprises one or more enzymes.

19. The composition of claim 9, further comprising one or more enzymes.

* * * * *